United States Patent
Topliffe et al.

(10) Patent No.: US 6,732,884 B2
(45) Date of Patent: May 11, 2004

(54) BULK MEDICATION DISPENSER AND MONITORING DEVICE

(76) Inventors: Douglas A. Topliffe, 24 Purgatory Rd., Mont Vernon, NH (US) 03057; Roger O. Topliffe, 606 Santa Margerita La., Punta Gorda, FL (US) 33950; Anil Sahai, 709 White Post Dr., Webster City, IA (US) 50595

( * ) Notice: Subject to any disclaimer, the term of this patent is extended or adjusted under 35 U.S.C. 154(b) by 473 days.

(21) Appl. No.: 09/791,067

(22) Filed: Feb. 22, 2001

(65) Prior Publication Data

US 2002/0113077 A1 Aug. 22, 2002

(51) Int. Cl.[7] .................................................. G07F 11/00
(52) U.S. Cl. ............................... 221/3; 221/10; 221/13; 221/15; 221/21; 221/121; 221/123; 221/133
(58) Field of Search ................................. 221/9, 10, 13, 221/21, 119, 121, 123, 133, 211, 254, 2, 3, 15

(56) References Cited

U.S. PATENT DOCUMENTS

| | | | | |
|---|---|---|---|---|
| 4,223,801 A | | 9/1980 | Carlson | |
| 4,572,403 A | | 2/1986 | Benaroya | |
| 4,573,606 A | * | 3/1986 | Lewis et al. ..................... | 221/2 |
| 4,674,651 A | * | 6/1987 | Scidmore et al. ............... | 221/3 |
| 4,695,954 A | | 9/1987 | Rose | |
| 4,725,997 A | | 2/1988 | Urquhart | |
| 4,768,177 A | | 8/1988 | Kehr | |
| 4,837,719 A | | 6/1989 | McIntosh | |
| 4,943,939 A | | 7/1990 | Hoover | |
| 4,970,699 A | | 11/1990 | Bucker | |
| 5,014,875 A | | 5/1991 | McLaughlin | |
| 5,020,037 A | | 5/1991 | Raven | |
| 5,152,422 A | | 10/1992 | Springer | |
| 5,159,581 A | | 10/1992 | Agans | |
| 5,200,891 A | | 4/1993 | Kehr | |
| 5,323,929 A | * | 6/1994 | Marlar ............................ | 221/3 |
| 5,329,459 A | | 7/1994 | Kaufman | |
| 5,347,453 A | | 9/1994 | Maestre | |
| 5,392,952 A | | 2/1995 | Bowden | |
| 5,412,372 A | | 5/1995 | Parkhurst | |
| 5,431,299 A | | 7/1995 | Brewer | |
| 5,441,165 A | * | 8/1995 | Kemp et al. .................... | 221/2 |
| 5,472,113 A | | 12/1995 | Shaw | |
| 5,490,610 A | * | 2/1996 | Pearson ......................... | 221/2 |
| 5,522,525 A | | 6/1996 | McLaughlin | |
| 5,562,232 A | | 10/1996 | Pearson | |
| 5,564,593 A | | 10/1996 | East | |
| 5,582,323 A | | 12/1996 | Kurtenback | |
| 5,609,268 A | | 3/1997 | Shaw | |
| 5,641,091 A | | 6/1997 | Daneshvar | |
| 5,646,912 A | | 7/1997 | Cousin | |
| 5,657,236 A | | 8/1997 | Conkright | |
| 5,765,606 A | * | 6/1998 | Takemasa et al. ........... | 221/2 X |
| 5,850,344 A | * | 12/1998 | Conkright .................. | 221/2 X |
| 5,971,594 A | | 10/1999 | Sahai | |
| 6,401,991 B1 | * | 6/2002 | Eannone ..................... | 221/2 X |

* cited by examiner

Primary Examiner—David H. Bollinger
(74) Attorney, Agent, or Firm—Davis & Bujold, P.L.L.C.

(57) ABSTRACT

A medication dispensing system comprising an on-site medication dispensing unit and a central monitoring facility. The on-site medication dispensing unit holds bulk amounts of medication in a plurality of separate receptacles from which it selects a desired medication dosage according to an entered and stored prescription regimen and then notifies the patient by an audible or other sensory signal. If the patient presses a button within a prescribed time, the unit dispenses the dosage. If the patient does not press the button within the prescribed time, or if the unit detects a failure to dispense the selected canister, the unit makes the receptacle inaccessible and contacts a predetermined list of caregivers and the central monitoring facility.

17 Claims, 7 Drawing Sheets

BULK MEDICATION DISPENSER AND MONITORING DEVICE

FIELD OF THE INVENTION

The present invention relates to a prescription medication dispensing apparatus for automatically effecting a physician prescribed medication program by selectively providing and withdrawing a prescribed dose of medication at desired times from a bulk medication loading format and also monitoring and communicating patient compliance with the medication program to a remote monitor or caregiver.

BACKGROUND OF THE INVENTION

Doctors commonly prescribe a regimen of pills to be taken by ill persons, for example, a regimen such as "take two of the blue pills every six hours and one of the green pills every four hours" or the like is not uncommon. For some persons, such a specific regimen or course of medication may be easily followed. For other persons however, confusion can arise both concerning the schedule and concerning whether or not the medication has been taken. This problem occurs frequently where a large number of different medications are prescribed or with elderly persons who may have suffered some loss of mental faculties.

A variety of automated dispensers of pills which are purportedly aimed at some aspects of this dispensing problem are described in the related art. According to their respective descriptions these dispensers are intended to provide for dispensing of pills according to some specified regimen. In addition, in some cases, they have some described means to permit a determination of deviations from their programmed regimen. These dispensers, however have shortcomings in their complexity, cost, flexibility, ease of use and error resistance for use in many conventional medication dispensing needs.

Many dispensers which overcome the above noted drawbacks are highly dependent upon attention and diligence by caregivers. Some apparatus require the caregiver to properly fill the medication cups and stack them in the appropriate order in the device for subsequent dispensing. Other apparatus require the care giver to place medication into small containers within the dispenser. Thus, the use of such a device requires substantial amounts of handling and effort by a knowledgeable caregiver which is expensive and susceptible to error.

SUMMARY OF THE INVENTION

Wherefore, it is an object of the present invention to overcome the above mentioned shortcomings and drawbacks associated with the prior art.

It is an object of this invention to provide an on-site medication dispensing unit that is readily programmable for dispensing pills to a patient over an extended period of time and which monitors patient compliance with the programmed medication regime.

Another object of this invention is to prevent overdosing or multiple dosages in the unit's output mechanism by having a visual and/or audible alerting feature which notifies the patient at a prescribed dosage time in accordance with the regimen that is programmed into the unit and then, and having a limited time window during which the patient must press a button or similar input device to activate the unit's output mechanism to effect a physical dispensing of the dosage from the unit. The time window is reprogrammable. If the patient has not pressed the button or activated the input device when the time window ends, the dosage is inaccessible to the patient. This missed medication can be reissued to the patient the following delivery or day if appropriate or will be locked away until the caregiver intervenes. A further feature of the unit alerts the patient in steps of escalating intensity, either audibly and visually, or both, if the button or similar input device is not activated.

It is another object of this invention to provide a medication dispensing unit which is directly linked to a 24-hour monitoring facility or directly to a caregiver if an occurrence that is defined by the unit's program to be an emergency situation arises. An example emergency situation is the patient's failure to activate the dispensing button which, as described above, causes the dosage to be inaccessible to the patient. If this occurs more than a predetermined number of times over a predetermined time duration, it would cause an alert to be sent directly to a caregiver and/or an alert to a monitoring facility.

Another object of the present invention is to provide a medication dispensing device which permits bulk loading of the device for at least a 30-day supply of medication.

A further object of the present invention is to provide a device which is capable of being resupplied from a chain pharmacy's managed care pharmacy division in a bulk loading format.

Yet another object of the present invention is to provide a bulk loading format where once the bulk medication is loaded in the device, no further human interaction with the medications is necessary to dispense the appropriate dosages of medications.

A still further object of the present invention is to select a desired prescribed medication dosage from the bulk loading format and deliver the dosage to the patient for only a prescribed period of time.

One embodiment of the on-site medication dispenser unit includes a rotating carousel wherein the canisters carried by the carousel may be loaded with at least a week's worth of a particular type of medication or types of medication. Anticipating when a medication dosage, or series of dosages is to be dispensed, the carousel is rotated so that the canister containing the appropriate pill is positioned at a selecting mechanism. The selecting mechanism selects a pill from the canister and drops it into a waiting receptacle, the selecting mechanism continues to select pills from individual canisters on the rotating carousel until a required dosage has been dropped into the receptacle.

At the prescribed dosage time the dispenser's program initiates an alert to the patient. As described above, when the patient is alerted, he/she is required to push a dispensing button within a programmable time window. If the button is pushed, the aligned receptacle releases its contents into a chute accessible to the patient. If the patient does not dispense the medication when alerted to do so, the dispenser first, for certain embodiments, steps through a progressive alerting of audio (tones and prerecorded voice messages) and visual alerts with increasing intensity, and if the medicine is not dispensed, the medication remains in the collection receptacle where it is inaccessible to the patient and the unit attempts to contact, in order, a preprogrammed list of caregivers and then if not successful, notifies the 24-hour central monitoring facility.

A still further embodiment of the invention provides a dispensing unit programmable to notify a patient to take a medication which is not dispensed by the unit. One example is the dispenser prompting the patient to take insulin using the above-identified visual display audible alarm and/or an audio message such as a prerecorded voice.

According to one example embodiment, the on-site dispensing unit is loaded by first filling the appropriate plurality of canisters, with the individual medication prescriptions, then transporting the filled canisters to the on-site unit, and loading them into the dispensing mechanism's canister carousel. The medication prescription canisters may be filled at the location of the on-site unit, or prefilled at a central distribution facility, or at a local station, such a place within a nursing home.

After loading the bulk medications into the canisters, the unit is programmed using one of the following three methods; call the central monitoring facility and have the unit programmed remotely, use a setup panel to select a preprogrammed standard, use a setup control panel to enter in a customized schedule.

A control panel for programming the dispensing unit is preferably located under a cover of the dispensing unit thereby, preventing accidental or other altering of the stored medication dosage schedule.

In addition to the medication dispensing and monitoring functions of the dispensing unit, a further embodiment includes a wireless communicating device worn by the patient which is communicatively linked with the dispenser to provide additional emergency protection to some patients. In an emergency, the patient can activate the wireless communication device which would communicate with the dispensing unit. The dispensing unit would, in turn, send an emergency message to the central monitoring station. The personal communication device may be.a pendant worn around the neck or any other suitable device that can be worn on the patients body. The medication dispensing unit may optionally incorporate an emergency button that serves the same function as the personal communication device. Other embodiments of the wireless emergency communications device are a wall mounted wireless emergency button and a table top wireless emergency button.

The present invention also relates to a medication preparation and dispensing apparatus for selecting and delivering at least one prescribed medication from a plurality of bulk medication amounts to a patient, the preparation and dispensing apparatus comprising a housing accommodating a plurality of receptacles containing the bulk medication amounts and a selection mechanism for obtaining the at least one prescribed medication from at least one of the plurality of receptacles, a medication dosage holder for collecting the at least one prescribed medication from the selection mechanism, a dispenser for dispensing the at least one medication collected by the medication dosage holder to the patient within a desired time period, and wherein a programmable computer instructs the selection mechanism to obtain the at least one medication from the bulk medication amounts and deliver the at least one medication to the dosage holder, the computer also communicating with the dispenser to issue the at least one medication to the patient within the desired time period.

BRIEF DESCRIPTION OF THE DRAWINGS

The invention will now be described, by way of example, with reference to the accompanying drawings in which.

DESCRIPTION OF THE PREFERRED EMBODIMENTS

Figure 1:
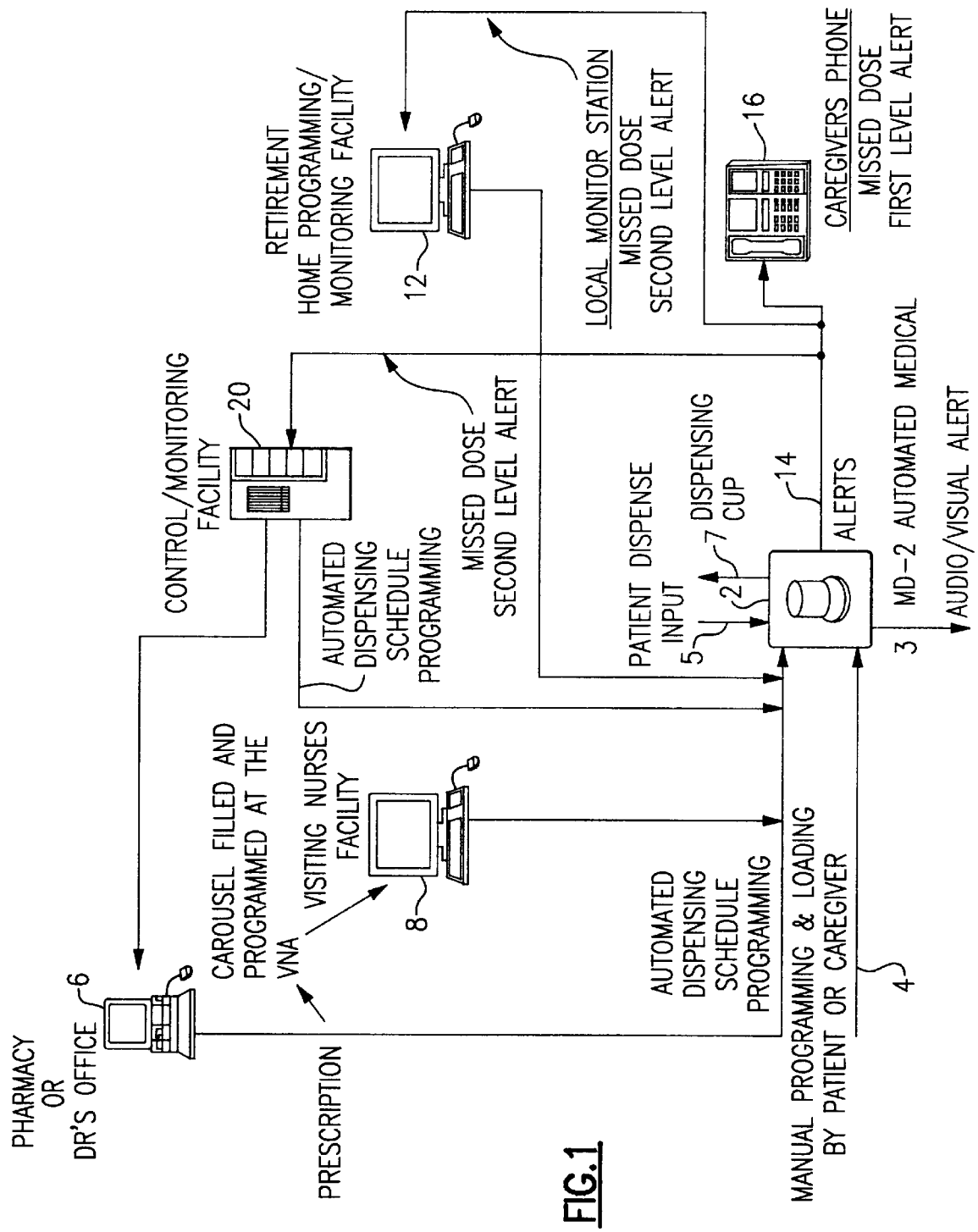
FIG. 1 is a schematic system diagram indicating the dispensing and monitoring functions of the medication delivery system.

FIG. 1 is a high level system diagram of an example medication dispensing and monitoring system according to the present invention. The FIG. 1 system includes an on-site medication dispenser 2 which stores a plurality of canisters described in detail further below, each canister filled with one or several pills of one type or prescription for dispensing at a prescribed time. The canisters can be individually loaded or preloaded with medication and loaded into the on-site dispensing unit 2 by authorized persons from a visiting nurse facility (VNA) 8 or from a doctors office 6, or by a pharmacy or local caregiver 4. The specific apparatus and details of operation of the medical dispensing unit 2 are described further below in reference to FIGS. 2–6.

The on-site dispensing unit 2 has a microprocessor-based controller 100, which is described further below, the controller 100 having a standard data storage function (not shown). The dispenser unit 2 data storage receives and stores a dispensing program, or receives data entries into a pre-stored user-prompt program, representing the patient's prescribed medication regimen. The program or data is entered into the unit 2 manually, by either the patient or the caregiver 4, or is received via a web based computer network from one of several remote sites including the patient's physician office 6, a nursing facility 8, a central control/monitoring facility 20, or a pharmacy.

The on-site dispensing unit 2 then, by its example apparatus and operation described below, executes the entered dispensing program by alerting the patient, by a visual and/or audible means 3, at each of the programmed dosing times and, concurrent with each alerting operation, places or assigns one of its internally selected and stored dosages into a ready-to-dispense mode or mechanical state. The controller 100 concurrently establishes a window of time, relative to the alerting signal, during which the patient can input a dispensing signal 5 via, for example, a button 31, shown in FIG. 2, or other input device, such as a touchscreen (not shown). The duration of the time window is set by the entered program or by a default value. If the user input signal 5 is received before expiration of the time window, the assigned dosage is output from the unit, as shown by label 7. The apparatus and method of the on-site dispensing unit 2 for carrying out the patient alerting and dispensing operations are described in further detail below.

If the patient has not yet responded, e.g. pushed the button 31 of the medication dispensing unit 2, at the end of the time window, the unit 2 for the FIG. 1 embodiment immediately transmits an alert 14 via, for example, a unit modem and telephone to a first designated caregiver 16. In addition to generating the alert 14, the on-site dispensing unit 2 prevent missed medication from being delivered to the patient for this dose period by an apparatus and operation described in further detail below.

If no response is received by the unit 2 from that first designated caregiver, the unit 2 sends another alert 14 to a second designated caregiver for instance a retirement/nursing home monitoring facility 12. Alerting sequences different from the example above are readily written into the dispenser unit 2 microprocessor-based controller 100 to achieve different priority sequences. A preferred example notifies the central monitoring facility when there is no valid response from any of the designated caregivers 16 or from the retirement home monitoring facility 12.

Instead of a unit 2 modem and a computer network system communication with the remote sites, such as 16, 12 and 20 can be realized by direct phone line or cellular phone connection. Regarding the specific form of receipt verification signal that the remote monitoring sites 16, 12 and 20 transmit back to the on-site dispensing unit 2, that is a simple design choice, with examples including a specific phone keypad entry, or sequence of entries, or a designated key (not shown). Further, the dispenser unit 2 may be equipped with a voice-recognition feature, recognizing, for example, "I'll be right over." Various commercial voice recognition hardware/software modules, readily incorporated into a standard microprocessor-based controller 100 are available as off-the-shelf items.

In the description above of the FIG. 1 example system, the on-site dispensing unit immediately transmits an alert signal 14 if there has been no user input of the dispensing signal when the time window ends. A further embodiment, uses a plurality of, for example, two time windows during which the user may input the dispensing signal, e.g. press the button 31. In that further embodiment, the audio or visual alarm is generated at a first intensity during the first time window. If that first time window ends and the user has not yet entered a dispensing signal, the unit increases the alarm level. The increased alarm level is continuous or, alternatively, is steadily increasing, until the end of the second time window. If the user, at the end of the second time window, has still not entered the dispensing signal then the unit 2 generates the alert signal 14 as described above.

Referring to FIG. 1, the central monitoring facility 20 is connected to the on-site medication dispenser 2 via a modem and the computer network system and, in addition to receiving alerts 14 from the unit 2, unit 2 is optionally programmed for periodic reporting concerning the operation and status of the unit 2. The information transmitted by such reporting is a design choice, preferably including a history of all dispensing operations over a set time period. In addition, the central monitoring facility may send a query to the on-site dispensing unit 2 over the computer system requesting information. Still, further, the patient's health care provider 6 may request a record of dosage schedule compliance from the central monitoring facility 20 to further enhance the treatment of the patient. Such records may be generated as hard paper copies or electronic files.

Figure 2:
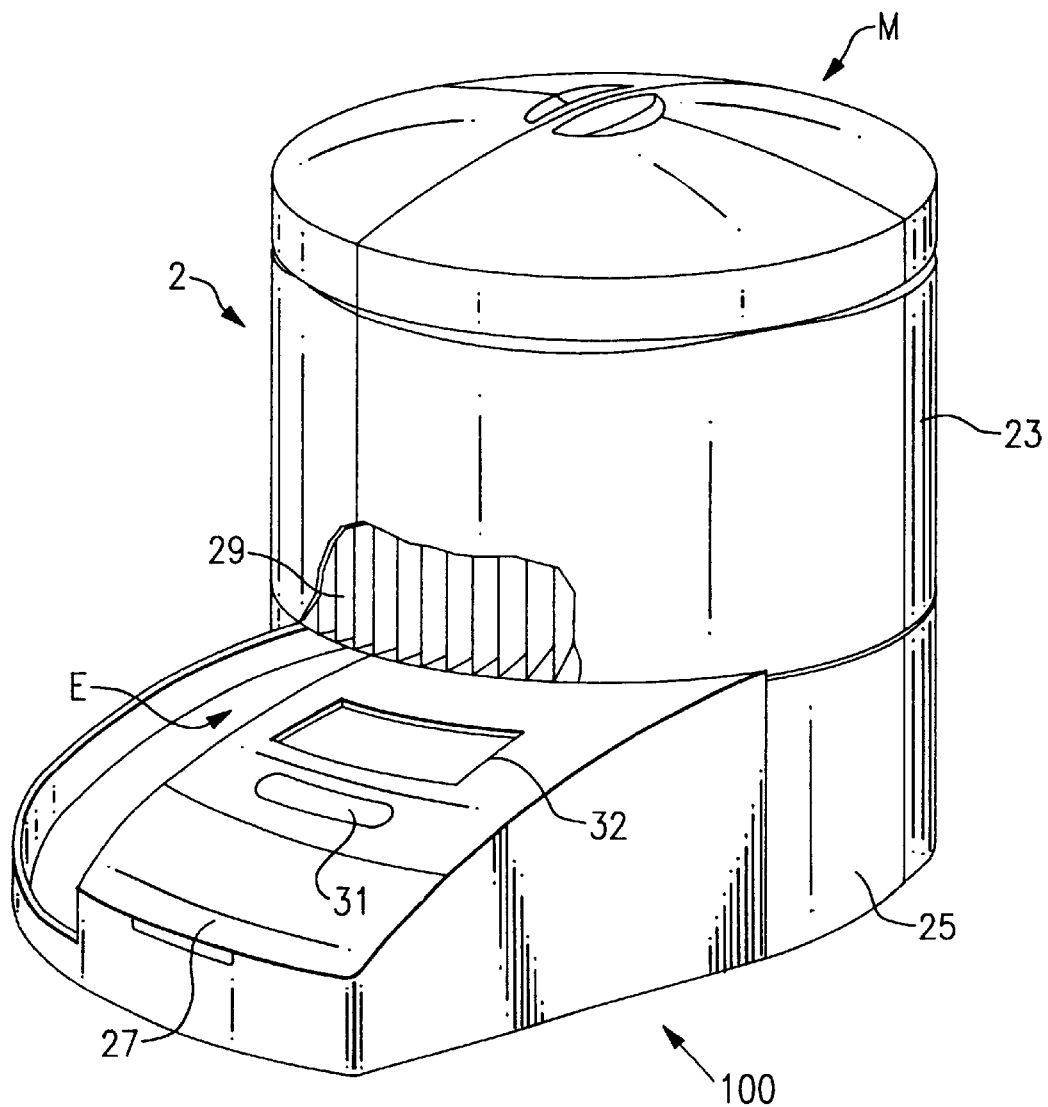
FIG. 2 is a perspective view of the complete bulk medication dispenser.

Turning now to FIG. 2, a general description concerning the medication dispensing unit 2 will now be provided. The medication dispensing unit 2 is a self contained, programmable and automated medication dispenser efficiently delivering at least a 30 day supply of medication to a patient with no human caregiver intervention. The unit 2 is functionally capable of selecting desired medications from a number of internal bulk pill bins or receptacles 21 within the apparatus and preparing a particular prescription for delivery to a patient at a desired programmed time. The unit 2 carries out these selection and dispensing functions in accordance with instructions programed into the controller 100 which also monitors patient compliance with the prescription regimen and communicates associated data to a remote caregiver via the central monitoring facility as previously described. A detailed description of the unit 2 follows below.

The dispensing unit 2 is encased within a removable housing cover 23 supported on a base 25. The cover 23 encloses and protects the medication delivery mechanisms, the bulk medications and the dispensing cups into which the selected medications are delivered. The housing cover 23 may be provided with an opening M in a top most portion of the cover for allowing the bulk medication to be loaded into the apparatus, alternatively, the cover 23 may be made removable from the base 25 in its entirety for the same purpose or for servicing. An exit opening E is provided in a lower portion of the cover 23 or alternatively in the base 25 as shown for enabling the patient to retrieve the required dose of selected medications from the unit 2.

Situated on the base 25, and easily accessible to a user is a manual keypad 27 for programming instructions into the controller 100. A visual indicator or warning light 29 may be provided to alert a user that a dosage is prepared and should be retrieved and a graphic display for any type of information pertinent to the particular function or dosage being delivered may be shown by a visual display window 32. A dispensing button 31 is also positioned on the base, actuation of the button enabling a user to dispense the currently available dosage through the exit E.

Figure 3:
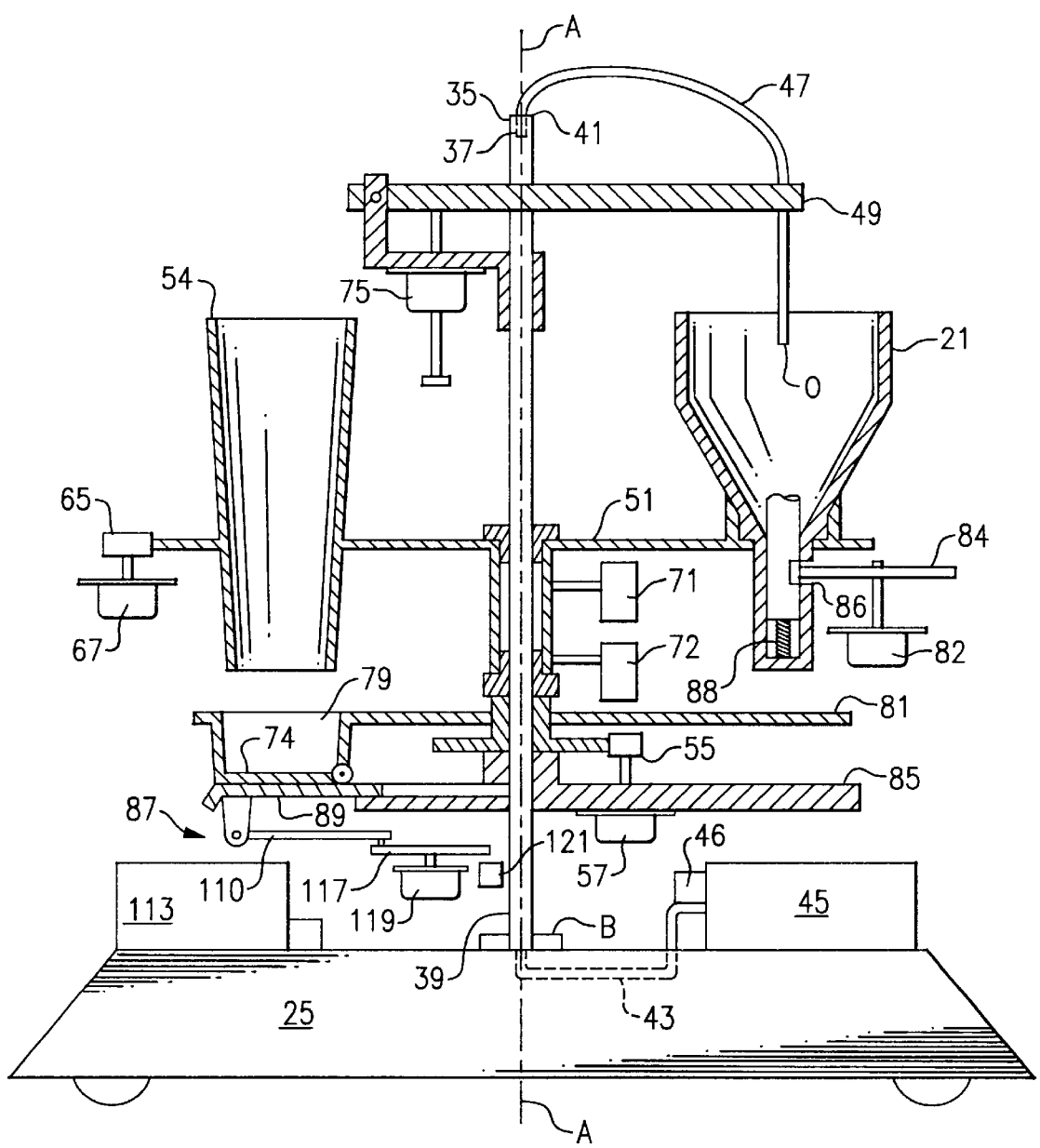
FIG. 3 is a cross sectional view of the internal pill manipulating mechanisms.

Turning to FIG. 3, the medication dispensing mechanisms contained within the housing cover 23 for preparing and dispensing a dosage will now be described. The base 25 provides support not only for the housing cover 23, but also for the internal medication dispensing mechanisms. Supported on the base 25 is a hollow center spindle 35 having a through passage 37 defined about a central axis A of the unit 2. The center spindle 35 extends vertically upward from a lower end 39, substantially supported at a central portion of the base 25, to a top end 41 spaced from the base 25.

At the lower end 39 of the center spindle 35, a communicating tube 43 is attached to enable the communication of a vacuum pump 45 contained within the housing cover 23 with the hollow passage 37 of the center spindle 35. A pressure sensor 46 is provided together with the vacuum pump to monitor vacuum pressure in the system by the internal computer 100. Increased vacuum pressure indicates pickup arm 47 picks a pill properly from container 21.

Connected to and communicating with the top end 41 of the center spindle 35 is a substantially flexible and vertically movable, hollow vacuum pickup arm 47. The vacuum pickup arm 47 has a first end having an outer diameter which slidably fits inside the through passage 37 to facilitate the vacuum pressure extending through the pickup arm 47 while enabling the first end of the pickup arm 47 fitted within the through passage 37 to be axially slidable therein.

A remainder of the pickup arm 47 extends from the top end 41 of the central spindle 35 and is provided with a substantially 180 degree bend turning a second end of the pickup arm 47 vertically downwards to define an opening O, which, when the vacuum pump 45 is turned on creating a vacuum through the hollow passage 37 causes suction at the opening O strong enough to retain a pill or desired medication dosage selected from one of the receptacles 21, a further description of which will be provided below.

The flexible pickup arm 47 is maintained as a 180 degree bend by a pickup arm support 49. The support 49 is a rigid arm extending horizontally from a first end portion having slidable engagement with the center spindle 35 to a second end portion spaced from the center spindle and supporting the second end of the pickup arm 47, specifically the opening O, in a desired pill engaging and retaining position. The support arm 49 is vertically moved up and down with respect to the center spindle 35 by a motor 75, it can be appreciated that this motor 75 may be any type as known in the art, but in this embodiment is a screw motor mounted on the spindle 35. As is to be appreciated, as the motor 75 raises and lowers the support arm 49, due to the inherent flexibility, the second end of the pickup arm 47, as well as opening O, secured at the second end of the support 49 is respectively vertically raised and lowered.

The opening O and the vacuum produced there engages and retains in general one pill at a time. Thus once a pill or medication is retrieved by the pickup arm 47, the pill or medication is subsequently dropped into a waiting container or cup before another pill or medication can be obtained. Because the pick up arm 47 is vertically movable, the receptacles 21 containing the individual medications must be positioned underneath the opening O to permit retrieval of the pill or medication.

Supported about the central axis A and the central spindle 35, a rotating carousel 51 supports and maneuvers a plurality of pill bins or receptacles 21 The carousel 51 is provided with a horizontally extending planer surface supporting the pill receptacles 21. The receptacles 21, which may be permanent or removable, are each capable of receiving and containing a bulk amount of a required medication. The receptacles 21 are supplied with the bulk medication via the medication supply entrance M or by removal of the cover 23. Each pill receptacle 21 is filled with a homogenous type of pill or medication such that when the opening O is brought into close proximity with the pills in a desired receptacle, only that type of pill can be engaged by the vacuum suction of the opening O. A further description of the pill receptacles 21 will be provided below.

The carousel 51 is rotatably driven about the central axis A by a carousel gear 65 located adjacent an outer rim of the carousel 51. The carousel gear 65 is connected to and driven by a carousel motor 67. Thus, the carousel motor 67, establishes direct control over the rotation of the carousel 51 and the positioning of the pill receptacles 21. In addition, to ensure the appropriate alignment of the receptacle 21 with the end 49 of the vacuum pick up arm, there is a position reader 71 which, via IR or any other means as is known in the art, is able to verify the correct positioning of the carousel 51 and the location of the desired receptacle 21 from which a dosage or medication is to be removed.

Figure 4A:
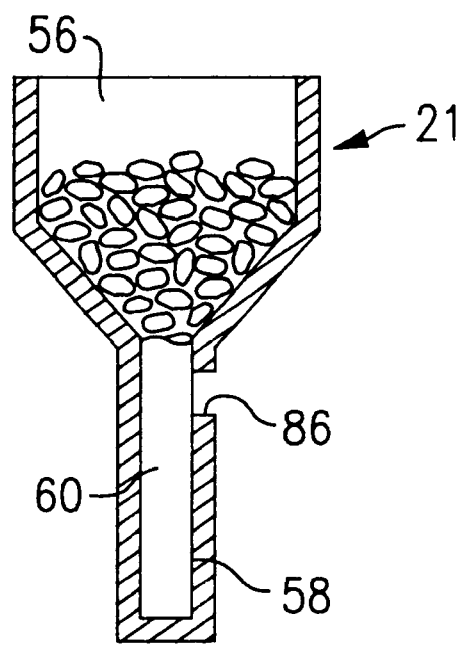
FIGS. 4A and 4B are cross sectional views of the pill receptacles of a first embodiment.

Turning now to FIGS. 4A and B, in the preferred embodiment of the invention, each pill receptacle 21 is designed having a main compartment 56 to which a bulk supply of a particular desired homogenous pill or medication can be supplied. The main compartment 56 may be of any desired size or volume to handle any number of desired pills or medications, the main compartment 56 can accommodate 0 to 500 pills, and usually about 50 to 300 and most preferably around 100–150 pills.

Each receptacle 21 is provided with an elongate vertically depending bottom cavity 58 at the bottom of the main compartment 56. The bottom cavity 58 contains a compression spring 88 biasing a plunger 60. The plunger has a first position wherein the plunger 60 is depressed and substantially withdrawn the main compartment 56. In a second position shown in FIG. 4A, the plunger moves from its first position and extends upward through the bulk medication, extracting at least one of the bulk loaded pills or medications to a supported position above the bulk pills on a top surface 62 of the plunger 60.

Figure 4B:
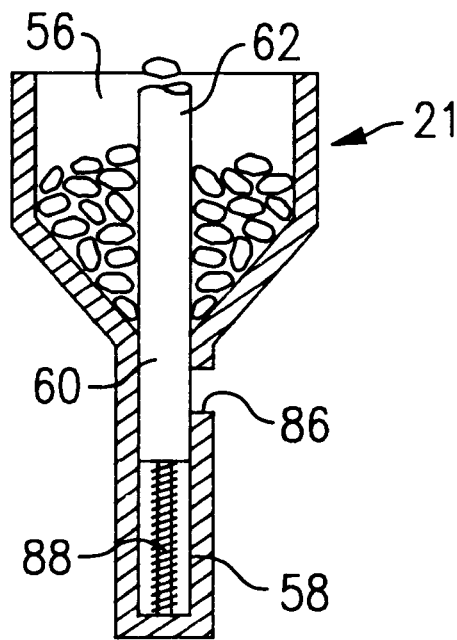

The extension of the plunger 60 pushes the extracted pill up above the bulk population of pills and brings it into close proximity of the opening O of the arm 47. The top surface 62 of the plunger 60 may be shaped with a particular pill size depression which assists in extracting and maintaining a pill thereon, and for placement of the pill in close proximity to the arm 47 and opening O. The bottom cavity 58 and plunger 60 may also be cooperatively threaded in order to provide a rotation for the plunger 60 as it extends upwards and through the bulk pill population facilitating the engagement of one pill positioned on the top surface 62 of the plunger 60 as depicted in FIG. 4B.

As shown in FIG. 3, the plunger 60 is actuated by a pill container motor 82 which drives a plunger gear 84. The plunger gear 84 extends through a slot 86 in the receptacle 21 engaging the plunger 60. It is to be appreciated as the plunger gear 84 rotates, engaging threads or notches (not shown) in the plunger 60, allowing the spring 88 to bias the plunger 60 upwards through the bulk population of pills. Once the plunger 60 has been fully extended and the pill removed therefrom by the arm 47 and opening O, the motor 82 reverses direction and the plunger gear 84 cooperatively changes direction, lowering the plunger 60 against the spring bias 88 down into the cavity 58 of the pill receptacle 21. Having engaged and retained a pill via the vacuum suction produced at opening O, the pickup arm 47 is raised to allow the carousel 51 to rotate to a subsequent position as described in greater detail below.

Figure 5A:
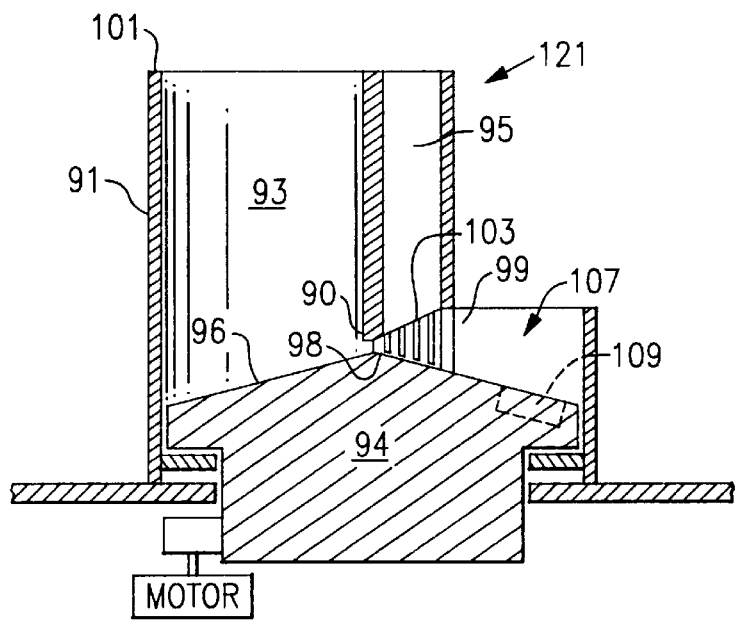
FIGS. 5A, 5B and 5C are a cross-sectional side view, a perspective view and a top planar view of a second pill receptacle embodiment.
Figure 5B:
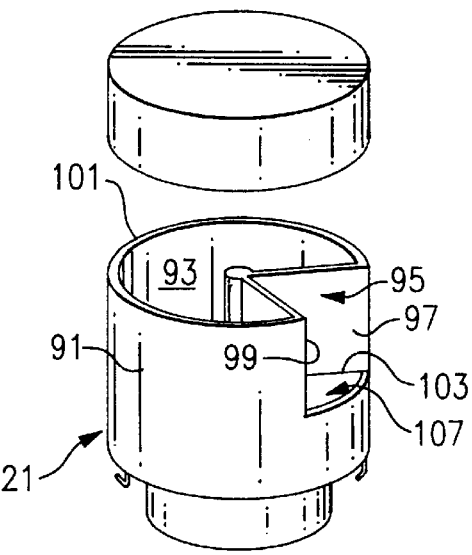
Figure 5C:
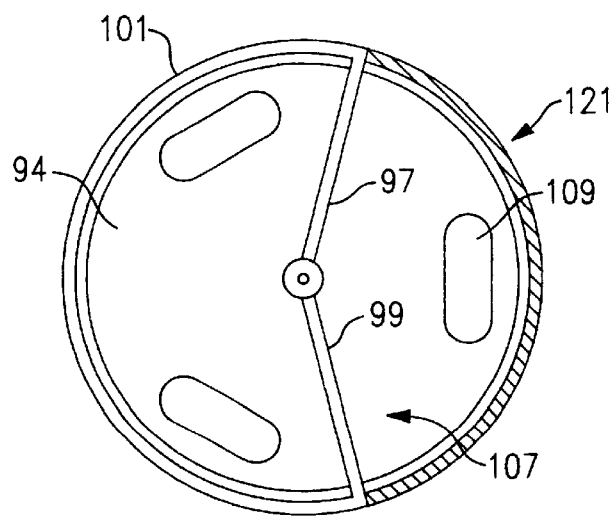

Turning now to FIGS. 5A, 5B, and 5C a second embodiment of the pill receptacle is provided. The receptacle 121 of the second embodiment is essentially a canister having a sidewall 91 defining a space 93 for containing the bulk medications. The receptacles can be provided with either a solid attached base 94 or base 94 can be a mixing drum which is capable of rotating relative to the sidewall 91, a further description of which will be provided below.

The sidewall 91 of each receptacle 121 is a modified cylinder having an upper portion and a lower portion. In the upper portion the sidewall 91 extends around in a cylindrical fashion between about 270–320 degrees. The cylinder is modified by an indentation 95 in the remaining 90-40 degrees. The indentation 95 is formed by a first and second planar walls 99, 97 extending inwardly from the sidewall 91 to a common intersection. The depending walls 99, 97 intersect with the sidewall 91 from a top edge or rim 101 of the sidewall 91 down to a point 65 between the sidewall rim 101 and the bottom edge 61 of the sidewall, the point being spaced a distance from the bottom edge 61 to form an opening 107 leading to a complete cylindrical lower pill pocket in the receptacle 121.

The lower portion of the sidewall 91 forms a complete cylinder surrounding the rotating base 94 and defines the pill retrieval area accessible through the opening 107. The rotating base 94 has a generally conical shaped surface 96 having a raised apex 98 in the center substantially vertically aligned with the intersection of the first and second planar walls 97 and 99. The conical shaped surface 96 provides for distribution of the pills toward the sidewall 91 of the receptacles 121. The conical surface 96 of the base 94 is also provided with an indentation or pill pocket 109 toward the sidewall 91 in the approximate size and shape of a single medication pill or tablet. This pill pocket 109 is sized to accommodate a pill or medication extracted from the bulk loaded portion 93 and deliver it into the pill retrieval area 107. The pill sits down in a defilade position in the pill pocket 109 and is carried out of the bulk loaded area 93 under the lower edge 92 of one of the first and second planar walls. This lower edge 103 is positioned close enough to the conical surface of the rotating base 94 to stop pills not in the pill pocket 109 from sliding into the pill retrieval area. Additionally, a device may be provided along the lower edge 92 to assist in preventing any pills other than that in the pocket 109 from entering into the pill retrieval area, such as a stiff bristle brush.

The opening 107 is the access point for the vacuum pick up arm to enter into proximity of the pill or medications extracted from the bulk loading area 93, and to retrieve a pill contained in the pill pocket 109 of the receptacle 121 when the container is rotated into the pick up position.

Figure 6A:
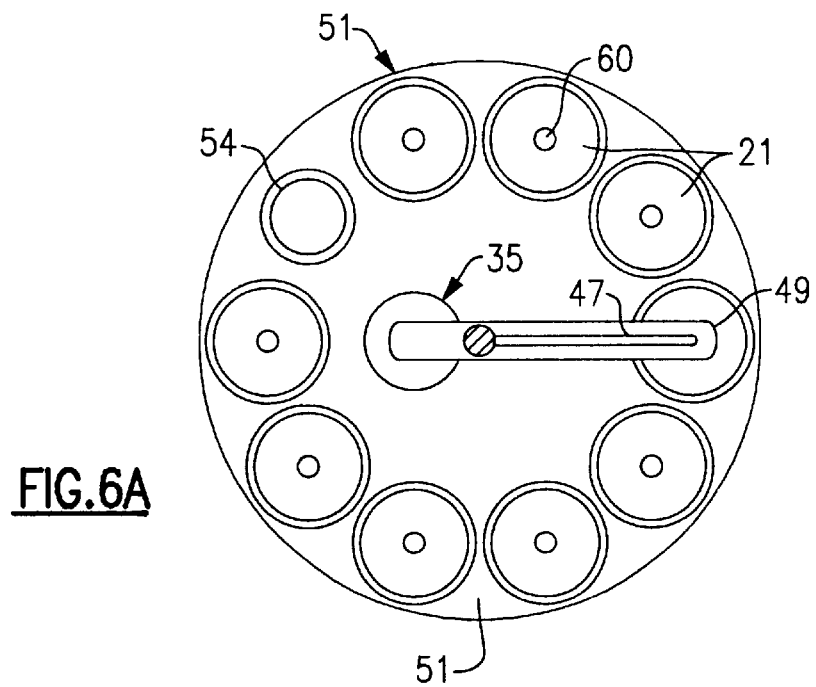
FIGS. 6A and 6B are top planar views of the pill receptacle carousel of a first and second embodiment respectively.

In one embodiment of the present invention shown in FIG. 6A, the carousel 51 is also provided with a drop chute 54. After engaging a pill, the support arm 49 and opening O is raised to allow the carousel 51 to rotate so that the drop chute 54 is positioned directly underneath the opening O and the pill retained thereon. When the vacuum is turned off the pill falls from the opening O into the drop chute 54 which directs the pill or medication into a dosage collection cup 79 located beneath the drop chute 54. Once the pill has been deposited in the dosage collection cup 79, the pick up arm 47, opening O and carousel 51 may be subsequently realigned to retrieve another pill or medication from a pill receptacle 21.

Figure 6B:
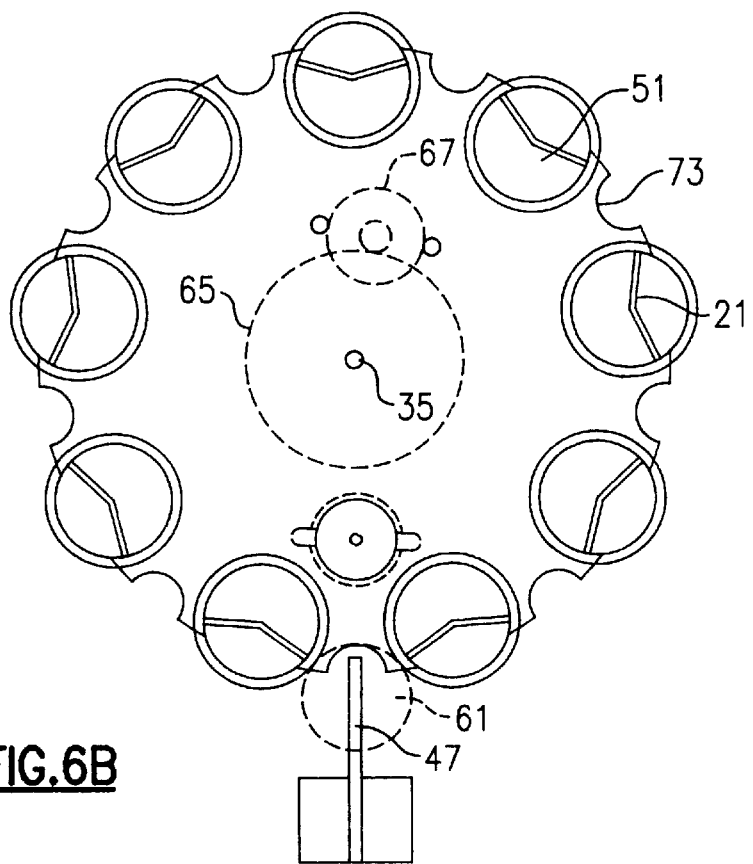

In another embodiment shown in FIG. 6B, any number of drop slots 73, a drop slot 73 being a passageway through the planer surface of the carousel 51, may be provided to allow the deposition of a pill in the collection cup 79. The drop slots 73 may be positioned adjacent and between each of the receptacle 21 and are also capable of being aligned with the end 49 of the vertical depending pick up arm 47 and verified by position sensor 71. After the vacuum pick up arm 47 has obtained a pill or dosage from the aligned receptacle 21, the motor 67 turns the gear 65 and thus the carousel 51 to position the drop slot 73 adjacent the receptacle 21 beneath the opening O of the pick up arm 47. The pill may then be dropped from the opening O and pass through the drop slot 54 to the pill collector cup 79.

Returning to FIG. 3, the vacuum pick up arm 47 works cooperatively with the rotation of the carousel 51. The pick up arm 47 has in general two positions: a first lower position for retrieving a pill from a receptacle 21, as shown in FIG. 3 and for dropping a pill through the drop chute 54 or drop slot 73, and a second upper position (not shown) wherein the pick up arm is positioned clear of any obstructions, i.e. the receptacles 21, so that carousel 51 can rotate to the next proper alignment. The vertical raising and lowering of the pick up arm 47 is driven by the screw motor 75 mounted on the center spindle 35 and having an upper and lower limit to ensure proper vertical alignment of the pick up arm 47 and specifically, the opening O for purposes of retrieving and dropping a pill.

The controller 100, generally an internal computer, in cooperation with the position sensors controls the coordination and cooperation of the motors and mechanisms described above. To prepare a dosage of medication, the controller 100 ensures the pick up arm 47 is in the upper position and the carousel 51, driven by the motor 67 is rotated until a receptacle 21 containing the required medication and dosage is properly aligned. Thus, the vertically depending end having the opening O of the pick up arm 47 is poised directly vertically above the pill receptacle 21. The optical position reader 71 verifies the positioning of the receptacle 21 with the controller 100 which then causes the vacuum pump 45 to be turned on. The pick up arm 47 is then lowered by the screw motor 75 until the arm attains a pill pick up level wherein the depending end and opening O are substantially inserted within the receptacle (as shown in FIG. 3). The vacuum force developed at the opening O of the vertically depending end of the pickup arm 47 then grabs the dosage of medication from the receptacle and/or the top surface 62 of the plunger 60 and the pressure sensor 46 located in conjunction with the communicating tube 43 detects whether the pill is retained on the pick up arm thus indicating that the controller 100 can continue operation.

The motor 75 then raises the pick up arm 47 holding the dosage to the second position. The carousel 51 is then rotated by the motor 67 to position the drop chute 54 or drop slot 73 immediately beneath the opening O, via the optical position sensor 71. The pickup arm 47 is lowered to the first lower position, and the vacuum pump 45 is turned off thus releasing the pill into the awaiting collector cup 79. Leaving the collector cup 79 in place, this process is then repeated for as many times as necessary to provide the required medication for a dosage into a single collection cup 79.

Located below the carousel 51 platform is a pill collector carousel 81 supporting at least one of the above described collection cups 79. The pill collector carousel 81 is also aligned about the central axis A and has a central through hole, through which the hollow central spindle 35 passes. The pill collector carousel 81 is rotatable relative to the central spindle and carousel 51 and is provided with at least a pill collector cup 79 for collection of medication dosages dropped from the vertically depending end of the vacuum pickup arm 47 as described previously, although it is foreseeable that any number of collection cups may be supported by the pill collector carousel 81.

The pill collector carousel 81 is a substantially planar surface having openings forming or supporting a rim of the collector cup 79 which may be permanent or removable or replaceable. The pill collector carousel 81 is provided with a pill collector carousel gear 55 which is driven by a pill collector carousel motor 57 so the pill collector carousel 81 is enabled to rotate relative to the center spindle 35 as well as the carousel 51. The pill collector carousel 81 positions the collection cup 79 beneath the opening O of the pick up arm and accepts the required dosage through the drop chute 54 or drop slot 73 from the pick up arm 47. The collection cup 79 remains in place as the above described process is repeated as many times as necessary in order to provide the required dosage, or number of pills to the collector cup 79.

The pill collector carousel motor 57 is also connected to the controller 100, and when the computer acknowledges the completion of a complete dosage delivered to the collection cup, the motor 57 rotates the pill collection cup to a position substantially adjacent the exit opening E of the housing which can be verified by a position sensor 72.

A sliding surface 85 is positioned below the pill collection carousel 51 and substantially supports a bottom of the pill collection cup 79. The bottom of the collector cup 79 may be provided with a hinged trap door 74. The door is supported during filling operations and during rotation of the collector carousel sliding on the sliding surface 85. The pill collector cups 79 are in contact with and allowed to slide across the sliding surface 85 as they are horizontally rotated by the pill collector carousel 81.

Adjacent the exit opening E, the sliding surface 85 is provided with a delivery opening 87. When a cup 61 encounters the opening 87, the trap door opens due to gravity and the weight of the pills, allowing the pills to be dispensed to the patient. The sliding surface 85 supports the cup vertically and ensures that the cup 61 is properly positioned, i.e. the mouth of the cup defines a substantially horizontal plane as the cup is positioned in the pill collector carousel 81. The sliding surface 85 is attached to the base 25 and also provides support and separation of the motors driving the pill collector carousel 81 and the carousel 51 from the medications and other delivery mechanisms.

Once the required dosage has been delivered to the collection cup 79 by the pick up arm 47 via either the drop chute 54 or drop slot 73, and the collection cup rotated by the collection cup carousel 81 to the appropriate position, a latch 110, connected with the patient dispense input 5, and operated thereby is provided whereby the dosage is only delivered if the patient operates the latch 110 via the input 5. A med tray 113 is provided in the base 94 of the unit 2 for receiving the allotted medications from the collection cup and providing the required medications to the patient. The collection cup containing the medication is positioned over the med tray 113 via rotation of the collection cup carousel when a time for supplying the medication is noted by the computer. The opening 87 of the sliding surface 85 is provided with a door 89 directly over the med tray 113, and directly beneath the collection cup 61 containing the desired medication positioned over the med tray 113.

The door 89 is connected to an offset cam 117 which is rotatably connected with a motor 119. When the motor 119 is instructed to open the door the motor 119 rotates the offset cam 117 which slides the latch away from the opening 87 in the sliding surface 85 and allows the medication to pour from the collection cup 61 into the med tray 113. The motor 119 may then close the door 89 by rotating the offset cam 117 in an opposite direction closing the door. An optical reader 121 may also be provided in conjunction with the door 89 to ensure the proper and complete opening and closing.

Where the patient fails to indicate that they are prepared to accept the medication, the door 89 will not open, and the contents of the collection cup are analyzed to ascertain if they can be either used for a subsequent dose or whether the dosage is to be removed from circulation.

Based on the programmed instructions provided to the controller 100 the operation and function of the unit 2 is conducted in the following manner.

Figure 7:
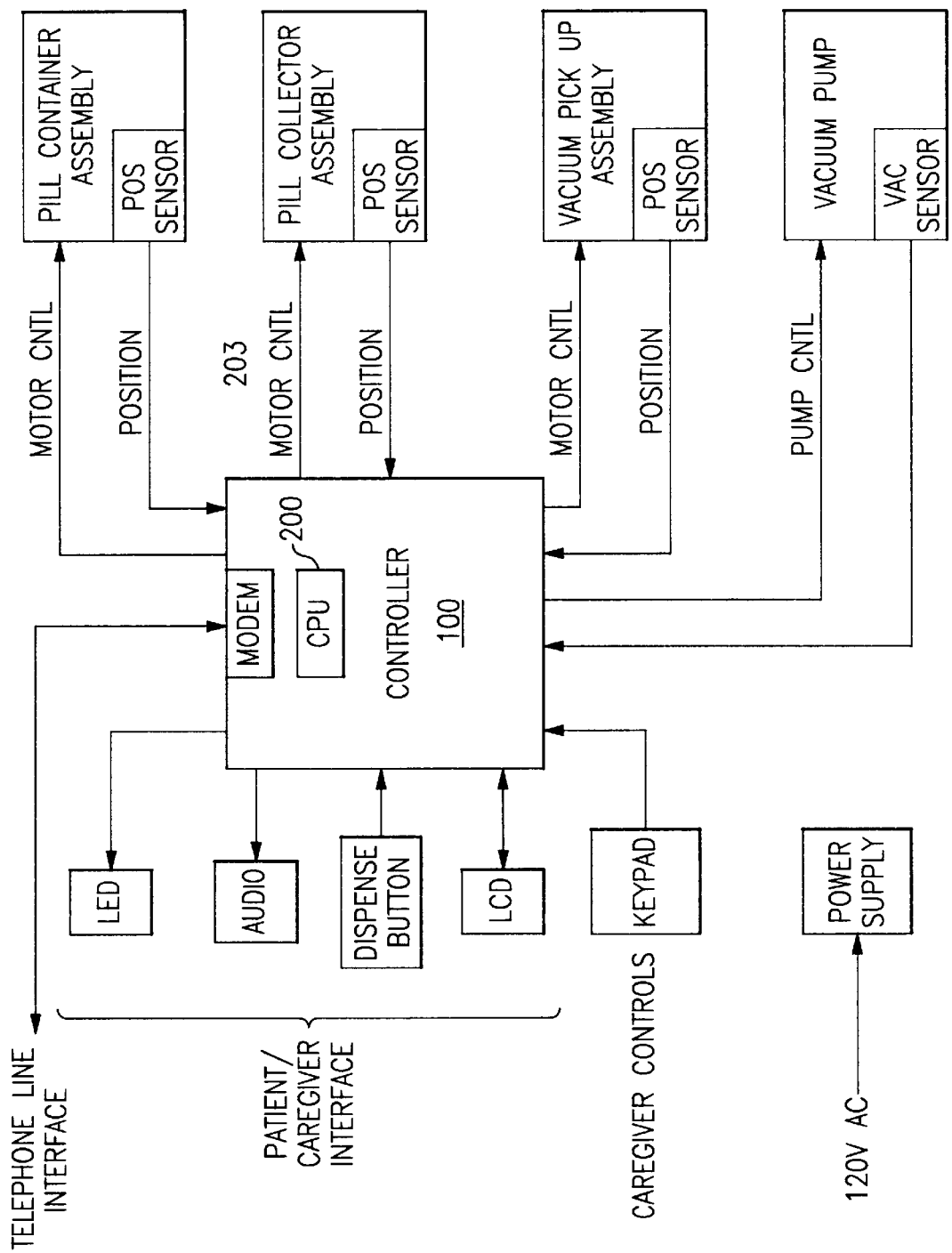
FIG. 7 is a block diagram of the functions of the apparatus computer controller.

FIG. 7 is a function block diagram of the controller 100 control of the aforementioned unit 2. The controller has a CPU 200 electronically coupled to a main motor control, controlling the rotation and availability of the pill receptacles 21. The controller 100 receives feedback from the position sensor of the carousel 23 and adjusts the motor control and hence the carousel 23 to accordingly align an appropriate receptacle 21 or drop slot 73. The main controller 100 also controls a collection cup carousel motor which rotates the appropriate collection cup 61 into the drop zone 52 beneath the receptacle carousel 23 in order to accept a retrieved medication from the pickup arm 47. A collection cup carousel position sensor is also related to the controller 100 in order to assure the collection cup carousel is properly aligned a collection cup 79 under the pick up arm 47. The main controller 100 also operates simultaneously and in conjunction with the main motor control and the collection cup carousel motor control a vacuum pickup motor control for retrieving and aligning the desired medications from the appropriate receptacles 21 to the proper collection cups 61. The vacuum pickup arm assembly 47 is also provided with a position sensor so that the controller 100 is aware of and able to coordinate the proper vertical positioning of the vacuum pickup arm assembly 47.

The main controller 100 also coordinates the activation and deactivation of the vacuum pump 45 for retrieval and release of the desired medications from the receptacles 21 into the collection cups 61, respectively.

The main controller 100 is generally supplied with a 120V AC power supplied to the controller 100 and respective motors and position sensors. The main controller 100 operates according to instructions imparted by a caregiver through a key pad 105. The key pad 105 may be either attached to the unit 2 or may also be remote therefrom. The main controller 100 further operates a liquid crystal display LCD for displaying a particular desired input information or output information to and from the controller 100 for either the patient or the caregiver. The main controller 100 is further connected with a dispense button 107 to which the patient has access to in order to retrieve the desired medications. The dispense button 31 is required to be operated before the appropriate medication is provided to the patient. To inform the patient that it period in which a medication is to be properly dispensed, an audio or visual signal may be put out by the controller 100 and unit 2 in order to alert the patient or caregiver. Thus the controller 100 may include a CPU having a microprocessor based CPU with internal memory to hold all software and scheduling information. The controller 100 also includes an imbedded Modem for communication between the controller 100 and an outside computer. The computer controls all electrotechnical elements of the machine including the vacuum pump and is provided with a battery backup for continued operation during any externally applied power failure.

Since certain changes may be made in the above described invention without departing from the spirit and scope of the invention herein involved, it is intended that all of the subject matter of the above description or shown in the accompanying drawings shall be interpreted merely as examples illustrating the inventive concept herein and shall not be construed as limiting the invention.

Wherefore, we claim:

1. A medication preparation and dispensing apparatus for selecting and delivering a prescribed medication from a plurality of bulk medication amounts to a patient, the preparation and dispensing apparatus comprising:

a housing accommodating a plurality of receptacles containing the bulk medication amounts and a selection mechanism for obtaining the prescribed medication from at least one of the plurality of receptacles;

a medication dosage holder for collecting the prescribed medication from the selection mechanism;

a dispenser for dispensing the medication collected by the medication dosage holder to the patient within a desired time period;

a programmable computer for instructing the selection mechanism to obtain the at least one medication from the bulk medication amounts and deliver the medication to the dosage holder, the computer also communicating with the dispenser to issue the at least one medication to the patient within the desired time period; and a base portion of the housing supporting a rotatable carousel carrying the plurality of receptacles and wherein each of said plurality of receptacles contains a homogenous quantity of medications.

2. The medication preparation and dispensing apparatus as set forth in claim 1, wherein upon instruction from the computer the carousel rotates the desired receptacle containing the homogenous quantity of medications to a retrieval position to facilitate the collection mechanism obtaining at least one medication therefrom.

3. The medication preparation and dispensing apparatus as set forth in claim 2, wherein the collection mechanism retrieves a medication from the receptacle and delivers the medication to the dosage holder.

4. The medication preparation and dispensing apparatus as set forth in claim 3, wherein after the collection mechanism retrieves a medication from the receptacle, the carousel rotates to a delivery facilitating position to facilitate the delivery of the medication to the dosage holder.

5. The medication preparation and dispensing apparatus as set forth in claim 4, wherein the carousel defines a through passage which is vertically aligned with the dosage holder in the delivery facilitating position to guide the medication to the dosage holder.

6. The medication preparation and dispensing apparatus as set forth in claim 5 wherein the suction tip has retrieved a medication and has moved to the higher second position with the medication, the carousel rotates to a delivery facilitating position wherein a through passage in the carousel is vertically aligned with the dosage holder, and the suction tip is caused to release the medication which is conveyed via the through passage into the dosage holder.

7. The medication preparation and dispensing apparatus as set forth in claim 1 further comprising a dispensing button communicating with the dispenser wherein when the dispensing button is activated the medication in the dispenser issues from the apparatus.

8. The medication preparation and dispensing apparatus as set forth in claim 7 wherein the dispensing button communicating with the dispenser can only activate the dispenser within the desired time period.

9. The medication preparation and dispensing apparatus as setforth in claim 7 wherein the dispensing button fails to activate the dispenser within the desired time period the medication in the dispenser is made inaccessible to the patient.

10. The medication preparation and dispensing apparatus as set forth in claim 9 wherein the medication having been made inaccessible is reissued to the patient at a subsequent desired time period.

11. The medication preparation and dispensing apparatus as set forth in claim 10 further comprising a communication link with a remote monitoring facility for alerting the remote monitoring facility when a particular number of medications have been made inaccessible to the patient.

12. The medication preparation and dispensing apparatus as set forth in claim 1 wherein the selection mechanism is a vacuum passage having a medication engaging suction tip for retrieving a medication from the receptacle.

13. The medication preparation and dispensing apparatus as set forth in claim 12 wherein the suction tip is vertically displaceable between a lower medication engaging position and a higher second position.

14. The medication preparation and dispensing apparatus as set forth in claim 1 wherein the computer communicates with and may be programmed with a desired medication prescription and the desired dispensing time periods via at least one of a central monitoring facility, a physician or care givers office, a pharmacy and a manual keypad input located on the housing of the apparatus.

15. The medication preparation and dispensing apparatus as set forth in claim 1 wherein each of the plurality of receptacles is provided with a medication selection plunger vertically biased against a bottom portion of the receptacle, for initially obtaining a medication and extending the medication for retrieval by the selection mechanism.

16. A method of medication dosage preparation and dispensing utilizing an apparatus for selecting and delivering a prescribed medication from a plurality of bulk medication amounts to a patient, the preparation and dispensing method comprising the steps of:

accommodating a plurality of receptacles containing the bulk medication amounts within a housing and obtaining the prescribed medication from at least one of the plurality of receptacles via a selection mechanism;

collecting the prescribed medication from the selection mechanism in a medication dosage holder;

dispensing the medication collected by the medication dosage holder through a dispenser to the patient within a desired time period;

providing a programmable computer to instruct the selection mechanism to obtain the medication from the bulk medication amounts and deliver the medication to the dosage holder, the computer also communicating with the dispenser to deliver the medication to the patient within the desired time period; and providing a base portion of the housing to support a rotatable carousel carrying the plurality of receptacles and wherein each of the plurality of receptacles contains a homogenous quantity of medications.

17. A medication preparation and dispensing apparatus for selecting and delivering a prescribed medication from a plurality of bulk medication amounts to a patient, the preparation and dispensing apparatus comprising:

a housing accommodating a plurality of receptacles containing the bulk medication amounts and a selection means for obtaining the prescribed medication from at least one of the plurality of receptacles;

a collection means for collecting the prescribed medication from the selection mechanism;

a dispensing means for dispensing the medication collected by the medication dosage holder to the patient within a desired time period; and wherein a programmable computer instructs the selection means to obtain the medication from the bulk medication amounts and deliver the medication to the collection means, the computer also communicating with the dispensing means to issue the medication to the patient within the desired time period.

* * * * *